United States Patent [19]

Tomioka et al.

[11] Patent Number: 4,843,090

[45] Date of Patent: Jun. 27, 1989

[54] SOIL FUNGICIDAL BENZIMIDAZOLES

[75] Inventors: Hiroki Tomioka, Takarazuka; Tadashi Ooishi, Toyonaka; Naonori Hirata, Sakai, all of Japan

[73] Assignee: Sumitomo Chemical Company, Limited, Osaka, Japan

[21] Appl. No.: 243,193

[22] Filed: Sep. 8, 1988

Related U.S. Application Data

[63] Continuation of Ser. No. 841,761, Mar. 20, 1986, abandoned.

[30] Foreign Application Priority Data

Jul. 5, 1985 [JP] Japan ................................. 60-148985

[51] Int. Cl.$^4$ ............................................. A01N 43/52
[52] U.S. Cl. ................................................. 514/388
[58] Field of Search ........................... 514/388; 548/306

[56] References Cited

U.S. PATENT DOCUMENTS 3,541,213  11/1970  Klopping ............................. 514/388
3,631,176  12/1971  Klopping ............................. 548/306
3,657,443   4/1972  Klopping ............................. 514/388

FOREIGN PATENT DOCUMENTS 1269970  4/1972  United Kingdom .
1346953  2/1974  United Kingdom .

OTHER PUBLICATIONS

Ann. Phytopath. Soc. Japan, vol. 49, 565–566 (1983).
Ann. Rept. Plant Prot. North Japan, vol. 35, 34–36 (1984).
Ann. Phytopath. Soc. Japan, vol. 48, 380 (1982).
Ann. Phytopath. Soc. Japan, vol. 51, 74–75 (1985).

*Primary Examiner*—Allen J. Robinson
*Assistant Examiner*—Raymond J. Henley, III
*Attorney, Agent, or Firm*—Stevens, Davis, Miller & Mosher

[57] ABSTRACT

A controlling composition for Fusarium diseases caused by the benzimidazole-resistant or sensitive strain of Fusarium which comprises as an active ingredient a benzimidazole derivative represented by the general formula (I) (hereinafter referred to as present composition),

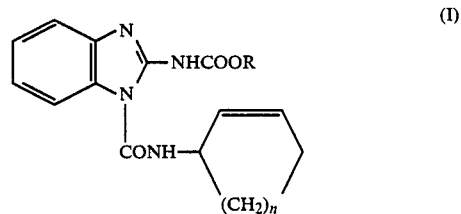

wherein R represents a $C_1$–$C_3$ lower alkyl group, and n represents 1, 2 or 3.

1 Claim, No Drawings

SOIL FUNGICIDAL BENZIMIDAZOLES

This application is a continuation of application Ser. No. 841,761, filed Mar. 20, 1986, now abandoned.

The present invention relates to a controlling composition for Fusarium diseases caused by the benzimidazole-resistant or sensitive strain of Fusarium which comprises as an active ingredient a benzimidazole derivative of the formula (I) (hereinafter referred to as present composition),

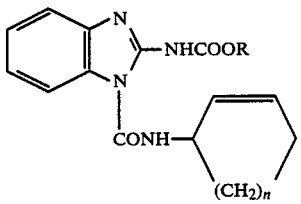

wherein R is a $C_1$–$C_3$ alkyl group, and n is 1, 2 or 3.

The control of Fusarium is an important subject in controlling soil-borne diseases. For controlling such diseases, there have been used a large number of benzimidazole compounds such as methyl 1-(butylcarbamoyl)-2-benzimidazolecarbamate (general name, Benomyl), methyl 2-benzimidazolecarbamate (general name, Carbendazim), 1,2-bis-(3-methoxycarboyl-2-thioureido)benzene (general name, Thiophanate-methyl), 2-(thiazol-4-yl)benzimidazole (general name, Thiabendazole), 2-(2-furyl)benzimidazole (general name, Fuberidazole), etc. In recent years, however, resistance to these pesticides, generally called resistance to benzimidazole, has occurred to become a problem. For example, with respect to "Bakanae" disease of rice plant which is one of Fusarium diseases, there are the following reports: Y. Kitamura, T. Hozumi and T. Tanaka, "Appearance of the Benomyl-resistant strain of *Fusarium moniliforme* ("Bakanae" disease) of rice plant", Annals of the Phytopathological Society of Japan, Vol. 48, pp. 380 (1982); K. Matsumoto, A. Hashimoto and T. Adachi, "Resistance to Benomyl of *Fusarium moniliforme* ("Bakanae" disease) of rice plant found in Fukushima Prefecture", Ann. Rept. Plant Prot. North Japan, Vol. 35, pp. 34–36 (1984); T. Takuda and T. Mishima, "Situation of the Appearance of Benomyl-resistant strain of *Fusarium moniliforme* ("Bakanae" disease) of rice plant in Shimane Prefecture", Annals of the Phytopathological Society of Japane, Vol. 51, pp. 74–75 (1985) and the like. Also, fusarium snow blight of wheat is reported in F. Tanaka, I. Saito, K. Miyajima, S. Tsuchiya and K. Tsuboki, "Generation of the Thiophanate-methyl-resistant strain of *Fusarium nivale* f. sp. *graminicola* (fusarium snow blight) of wheat", Annals of the Phytopathological Society of Japan, Vol. 49, pp. 565–566 (1983) and the like.

The present inventors searched for pesticides having a high controlling effect on not only benzimidazole-sensitive but also benzimidazole-resistant strains of Fusarium which cause Fusarium diseases, and as a result, unexpectedly found that the benzimidazole derivative represented by the general formula (I) belonging to a group of benzimidazoles has a very high controlling effect on the both strains at low dosage levels. The present inventors thus completed the present invention.

Fusarium causing soil-borne diseases, seed-borne diseases, etc. on which the present composition has excellent controlling effect include the followings: *Fusarium oxysporum* f. sp. *lycopersici* (fusarium wilt) of tomato, *Fusarium oxysporum* f. sp. *raphini* (yellows) of Japanese radish, *Fusarium oxysporum* f. sp. *cucumerinum* (fusarium wilt) of cucumber, *Fusarium oxysporum* f. sp. *niveum* (fusarium wilt) of watermelon, *Fusarium oxysporum* f. sp. *conglutinans* (yellows) of cabbage, *Fusarium oxysporum* f. sp. *fragariae* (yellows) of strawberry, *Fusarium nivale* f. sp. *graminicola* (fusarium snow blight) of wheat, *Fusarium roseum* f. sp. *cerealis* (fusarium blight) of wheat, *Fusarium oxysporum* f. sp. *vasinfectum* (fusarium wilt) of cotton, *Fusarium solani* f. sp. *phaseoli* (fusarium root rot) of kidney beans, *Fusarium solani* f. sp. *pisi* (root rot) of pea, *Fusarium moniliforme* ("Bakanae" disease) of rice, *Fusarium oxysporum* f. sp. *asparagi* (fusarium wilt) of asparagus, *Fusarium oxysporum* f. sp. *dianthi* (wilt) of carnation, *Fusarium oxysporum* f. sp. *cyclaminis* (fusarium wilt of cyclamen, *Fusarium oxysporum* f. sp. *tulipae* (bulb rot) of tulip and the like.

Of these pathogens, those having resistance to benzimidazole are *Fusarium oxysporum* f. sp. *lycopersici* of tomato, *Fusarium oxysporum* f. sp. *cucumerinum* of cucumber, *Fusarium oxysporum* f. sp. *fragariae* of strawberry, *Fusarium nivale* f. sp. *graminocola* of wheat, *Fusarium oxysporum* f. sp. *vasinfectum* of cotton, *Fusarium moniliforme* of rice, *Fusarium oxysporum* f. sp. *dianthi* of carnation and the like.

Of the compounds represented by the general formula (I), preferred ones are those in which R is a methyl, ethyl or isopropyl group and n is 2 or 3, more preferred ones are those in which R is a methyl or ethyl group and n is 2. Further more preferred ones include methyl 1-(2-cyclohexenylcarbamoyl)-2-benzimidazolecarbamate, methyl 1-(2-cycloheptenylcarbamoyl)-2-benzimidazolecarbamate, etc.

The benzimidazole derivatives represented by the general formula (I) can be produced:

(1) by reacting a 2-benzimidazolecarbamate of the formula (II),

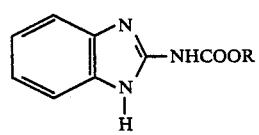

wherein R is as defined above, with a 2-cycloalkenylisocyanate of the formula (III),

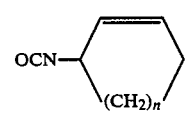

wherein n is as defined above, of, generally, 1 equivalent based thereon at 0° C. to 150° C. for less than 24 hours with or without a solvent, or (2) by reacting a 1-chlorocarbonyl-2-benzimidazolecarbamate of the formula (IV),

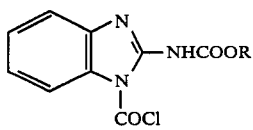

wherein R is as defined above, with 2-cycloalkenylamine of the formula (V),

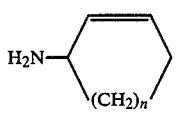

wherein n is as defined above, of, generally, 1 to 2 equivalents based thereon at 0° C. to 150° C. for less than 24 hours with or without a solvent in the presence of a dehydrochlorinating agent of 1 to 2 equivalents based on the compound (IV).

In these methods, two starting compounds, 2-benzimidazolecarbamate (II) and 1-chlorocarbonyl-2-benzimidazolecarbamate (IV), can easily be produced by the methods described in U.S. Pat. Nos. 3,657,443 and 3,541,213, respectively.

The solvent used in the present invention includes for example aliphatic hydrocarbons (e.g. hexane, heptane, ligroin, petroleum ether), aromatic hydrocarbons (e.g. benzene, toluene, xylene), halogenated hydrocarbons, (e.g. chloroform, carbon tetrachloride, dichloroethane, chlorobenzene, dichlorobenzene), ethers (e.g. diethyl ether, diisopropyl ether, dioxane, tetrahydrofuran, ethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate, diethyl carbonate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, N,N-dimethylacetamide), sulfur compounds (e.g. dimethyl sulfoxide, sulfolane) and mixtures thereof.

The dehydrochlorinating agent used in the present invention includes for example organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide) and the like.

After completion of the reaction, the benzimidazole derivative of the formula (I) is obtained, for example, by filtering off insoluble matters and concentrating the filtrate. If necessary, the product is purified, for example, by column chromatography, recrystallization, etc.

Production of the benzimidazole derivative of the formula (I) will be illustrated withh reference to the following reference example.

Reference example

To a mixture of 19.1 g of methyl 2-benzimidazolecarbamate and 600 ml of chloroform was added 13.7 g of 2-cycloheptenylisocyanate at room temperature (ca. 20° C.) with stirring. After stirring at room temperature for further 24 hours, the deposited crystal was filtered off, and the filtrate was concentrated under reduced pressure. The residue was purified by column chromatography on silica gel with chloroform as an eluent to give 8.2 g of methyl 1-(2-cycloheptenylcarbamyol)-2-benzimidazolecarbamate [compound (1)].

m.p. >300° C.

NMR (CDCl$_3$): δ(ppm) 1.24–2.38(m, 8H), 3.72(s, 3H), 4.34–4.74(m, 1H), 5.47–5.90(m, 2H), 6.92–7.36(m, 3H), 8.07–8.39(m, 1H), 10.22–10.52(m, 1H).

In the same manner as above, methyl 1-(2-cyclohexenylcarbamoyl)-2-benzimidazolecarbamate [compound (2)] was obtained from methyl 2-benzimidazolecarbamate and 2-cyclohexenylisocyanate.

m.p. >300° C.

NMR (CDCl$_3$): δ(ppm) 1.50–2.32(m, 6H), 3.80(s, 3H), 4.40–4.74(m, 1H), 5.69–6.02(m, 2H), 7.14–7.45(m, 3H), 8.28–8.58(m, 1H), 10.14–10.49(m, 1H)

Some of the compounds produced by the foregoing methods will be shown in Table 1.

TABLE 1

| Compound No. | R | n | Physical constant |
|---|---|---|---|
| (3) | CH$_3$ | 1 | m.p. >300° C. |
| (4) | C$_2$H$_5$ | 1 | m.p. >300° C. |
| (5) | n-C$_3$H$_7$ | 1 | m.p. >300° C. |
| (6) | i-C$_3$H$_7$ | 2 | m.p. 180–186° C. (dec.) |
| (7) | C$_2$H$_5$ | 2 | m.p. >300° C. |
| (8) | n-C$_3$H$_7$ | 2 | m.p. 140–144° C. |
| (9) | i-C$_3$H$_7$ | 2 | m.p. 90–92° C. |
| (10) | C$_2$H$_5$ | 3 | m.p. >300° C. |
| (11) | n-C$_3$H$_7$ | 3 | m.p. 167–194° C. |
| (12) | i-C$_3$H$_7$ | 3 | n$_D^{21}$ 1.5552 |

The present composition is generally used in the form of wettable powders, suspension formulations, granules, dusts, fine granules, etc. by mixing with solid carriers, liquid carriers, surface active agents and other auxiliaries for formulation.

These preparations are produced by the common formulation methods so that they contain 0.1 to 99.9 wt.%, preferably 0.2 to 80 wt.% of the benzimidazole derivative of the formula (I) as an active ingredient.

In the present invention, the solid carrier includes for example fine powders of granules of kaolin clay, attapulgite clay, bentonite, terra abla, pyrophyllite, talc, diatomaceous earth, calcite, walnut shell powder, urea, ammonium sulfate, synthetic hydrated silicon dioxide, etc. The liquid carrier includes for example vegetable oils (e.g. soybean oil, cotton seed oil), dimethyl sulfoxide, water, etc. The surface active agent used for emulsification, dispersion wetting, etc. includes for example anionic surface active agents such as the salt of alkyl sulfate, alkyl(aryl)sulfonates, dialkyl sulfo-succinates, the salt of polyoxyethylene alkylaryl ether phosphoric acid ester, naphthalenesulfonic acid/formalin condensates, etc., and nonionic surface active agents such as polyoxyethylene alkyl ether, polyoxyethylene alkylaryl ether, polyoxyethylene polyoxypropylene block copolymers, sorbitan fatty acid esters, polyoxyethylene sorbitan fatty acid esters, etc. The auxiliary for formulation includes for example lignosulfonates, alginates, polyvinyl alcohol, gum arabic, CMC (carboxymethyl cellulose), PAP (isopropyl acid phosphate), etc.

Formulation examples will be shown. Parts in the examples are by weight.

Formulation example 1

Fifty parts of the compound (1), 3 parts of calcium lignosulfonate, 2 parts of sodium lauryl sulfate and 45 parts of synthetic hydrated silicon dioxide are well pulverized and mixed together to obtain a wettable powder.

Formulation example 2

Two parts of the compound (2), 1 part of synthetic hydrated silicon dioxide, 2 parts of calcium lignosulfonate, 30 parts of bentonite and 65 parts of kaolin clay are well pulverized and mixed together, well kneaded with water, granulated and dried to obtain a granule.

Formulation example 3

Twenty-five parts of the compound (2), 3 parts of polyoxyethylene sorbitan monooleate, 3 parts of CMC and 69 parts of water are mixed and wet-pulverized until the particle size is reduced to less than 5 microns to obtain a suspension formulation.

Formulation example 4

Two parts of the compound (1), 88 parts of kaolin clay and 10 parts of talc are well pulverized and mixed together to obtain a dust.

Formulation example 5

Thirty parts of the compound (1) is mixed with and dissolved in dimethyl sulfoxide, and the solution obtained is adsorbed to and impregnated into 70 parts of attapulgite clay and dried to obtain a fine granule.

Formulation example 6

Ten parts of the compound (2), 14 parts of polyoxyethylene styrylphenyl ether, 6 parts of calcium dodecylbenzenesulfonate, 30 parts of xylene and 40 parts of isopropanol are well mixed to obtain an emulsifiable concentrate.

These preparations, either as such or as aqueous dilute solutions, are used for foliar treatment, seed treatment, seedling treatment, soil treatment, etc. Also, they may be used in mixture with other fungicides, insecticides, acaricides, nematocides, herbicides, plant growth regulators, fertilizers and soil improvers.

In paddy fields, upland fields, orchards, pastures, turfs, etc. wherein Fusarium causing soil-borne diseases, seed-borne diseases lives, the present composition may also be used as a controlling agent for Fusarium diseases caused by the benzimidazole-resistant or sensitive strain of Fusarium.

The dosage rate of the benzimidazole derivative of the formula (I), the active ingredient of the present composition, is generally 0.0001 to 10 kg/10 ares, preferably 0.001 to 5 kg/10 ares. When wettable powders, suspension formulations, etc. are used in dilution with water, the application concentration of the derivative is 0.0005 to 2.0%, preferably 0.005 to 0.5%, and granules, dusts, etc. are used as such without dilution. The seed treatment includes dressing treatment, dipping treatment, etc. The application concentration of the derivative is generally 0.05 to 2% per dry seed weight for dressing treatment, and 0.005 to 2% per dipping solution weight for dipping treatment.

Test examples of the present composition will be shown. Hereupon, compounds used as a control are shown by compound symbol in Table 2.

TABLE 2

| Compound symbol | Chemical structure | Remark (name) |
|---|---|---|
| A | benzimidazole-NHCOOCH$_3$ with N-CONH-cyclohexyl | Compound described in U.S. Pat. No. 3,541,213. |
| B | benzimidazole-NHCOOC$_2$H$_5$ with N-CONHC$_2$H$_5$ | Compound described in U.S. Pat. No. 3,541,213. |
| C | benzimidazole-NHCOOCH$_3$ with N-CONHC$_4$H$_9$(n) | Benomyl |
| D | phenyl with two NH—C(=S)—NH—COOCH$_3$ groups (ortho) | Thiophanate-methyl |

TABLE 2-continued

| Compound symbol | Chemical structure | Remark (name) |
|---|---|---|
| E | [benzimidazole]-NHCOOCH$_3$ | Carbendazim |

Hereupon, the controlling activity is indicated by the numerical value of "control of disease (%)" obtained as follows: The condition of disease of test plants on examination, i.e. the degrees of the colony and infected area on the leaves, stems, roots, etc. are observed with the naked eyes and classified into five grades of "disease index" are described below, and then "disease severity (%)" and "control of disease (%)" are calculated from the following equations.

| Disease index | Degrees of colony and infected area |
|---|---|
| 0 | No colony nor infected area is observed. |
| 0.5 | About 5% of colony or infected area is observed. |
| 1 | About 20% of colony or infected area is observed. |
| 2 | About 50% of colony or infected area is observed. |
| 4 | More than about 50% of colony or infected area is observed. |

$$\text{Disease severity (\%)} = \frac{\Sigma\left[(\text{disease index}) \times \binom{\text{number of examined seedlings}}{}\right]}{(\text{number of examined seedlings}) \times 4} \times 100$$

$$\text{Control of disease (\%)} = 100 - \frac{\text{disease severity in treated plot}}{\text{disease severity in untreated plot}} \times 100$$

Test example 1

Controlling test on yellows of Japanese radish (*Fusarium oxysporum* f. sp. *raphani*)

Upland field soil and infested soil containing cultured benzimidazole-sensitive strains of *Fusarium oxysporum* f. sp. *raphani* were well mixed and filled in plastic pots. Twenty seeds of Japanese radish (var., Wase-40 nichi) were sowed in each pot and covered with soil. Thereafter, the wettable powder of the test compound prepared according to Formulation example 1 was diluted with a prescribed amount of water, and the soil was drenched with the aqueous dilute solution. The seedlings were cultivated for 3 weeks in a greenhouse, and the controlling activity was examined. The result is shown in Table 3.

TABLE 3

| Test compound | Dosage rate of active ingredient (g/10 ares) | Control of disease (%) |
|---|---|---|
| (1) | 200 | 96 |
| (2) | 200 | 100 |
| (3) | 200 | 91 |
| (4) | 200 | 91 |
| (5) | 200 | 90 |
| (6) | 200 | 89 |
| (7) | 200 | 95 |
| (8) | 200 | 93 |
| (9) | 200 | 93 |
| (10) | 200 | 98 |
| (11) | 200 | 98 |
| (12) | 200 | 96 |

TABLE 3-continued

| Test compound | Dosage rate of active ingredient (g/10 ares) | Control of disease (%) |
|---|---|---|
| A | 400 | 10 |
| B | 400 | 15 |
| C | 400 | 18 |
| D | 400 | 12 |
| E | 400 | 13 |

Test example 2

Controlling test on yellows of Japanese radish (*Fusarium oxysporum* f. sp. *raphani*)

The test plots were inoculated with a wheat bran medium containing cultured benzimidazole-sensitive strains of *Fusarium oxysporum* f. sp. *raphani* at a rate of 500 g/plot (10 cm$^2$), and the soil was mixed with a prescribed amount of the fine granule of the test compound prepared according to Formulation example 5. Thereafter, Japanese radish (var., Taibyo-sofutori) was seeded at a rate of 3–4 seeds/hole (50 holes/plot). After two weeks, the seedlings were thinned to 1 seedling/hole (50 seedlings/plot) and then cultivated for further 5 weeks. The controlling activity was then examined. The result is shown in Table 4.

TABLE 4

| Test compound | Dosage rate of active ingredient (g/10 ares) | Control of disease (%) |
|---|---|---|
| (1) | 2000 | 85 |
| (2) | 2000 | 90 |
| (3) | 2000 | 82 |
| (4) | 2000 | 82 |
| (5) | 2000 | 81 |
| (6) | 2000 | 80 |
| (7) | 2000 | 84 |
| (8) | 2000 | 84 |
| (9) | 2000 | 83 |
| (10) | 2000 | 89 |
| (11) | 2000 | 88 |
| (12) | 2000 | 86 |
| A | 4000 | 10 |
| B | 4000 | 12 |
| C | 4000 | 8 |
| D | 4000 | 9 |
| E | 4000 | 11 |

Test example 3

Controlling test on root rot of pea (*Fusarium solani* f. sp. *pisi*)

Upland field soil and infested soil containing cultured benzimidazole-sensitive strains of *Fusarium solani* f. sp. *pisi* were well mixed and filled in plastic pots. Thereafter, the seeds of pea (var., 30-nichi kinusaya) dressed with a prescribed amount of the wettable powder of the test compound prepared according to Formulation example 1 were sowed at a rate of 20/pot and covered with soil. The seedlings were cultivated for 4 weeks in a greenhouse, and the controlling activity was examined. The result is shown in Table 5.

TABLE 5

| Test compound | Dosage rate of active ingredient (g/kg of dry seed) | Control of disease (%) |
|---|---|---|
| (1) | 1 | 96 |
| (2) | 1 | 96 |
| (3) | 1 | 91 |
| (4) | 1 | 91 |
| (5) | 1 | 90 |
| (6) | 1 | 89 |
| (7) | 1 | 95 |
| (8) | 1 | 93 |
| (9) | 1 | 93 |
| (10) | 1 | 94 |
| (11) | 1 | 94 |
| (12) | 1 | 93 |
| A | 1 | 24 |
| B | 1 | 18 |
| C | 1 | 15 |
| D | 1 | 16 |
| E | 1 | 14 |

Test example 4

Controlling test on "Bakanae" disease of rice (*Fusarium moniliforme*)

Unhulled seeds of rice (var., Sasanishiki), infested with benzimidazole-resistant strains of *Fusarium moniliforme*, were dressed with a prescribed amount of the wettable powder of the test compound prepared according to Formulation example 1, and 50 dressed seeds were sowed on nursery soil and covered with soil. The seedlings were cultivated for 4 weeks in a greenhouse, and the controlling activity was examined. The result is shown in Table 6.

TABLE 6

| Test compound | Dosage rate of active ingredient (g/kg of dry seed) | Control of disease (%) |
|---|---|---|
| (1) | 1 | 100 |
| (2) | 1 | 100 |
| (3) | 1 | 92 |
| (4) | 1 | 92 |
| (5) | 1 | 91 |
| (6) | 1 | 90 |
| (7) | 1 | 98 |
| (8) | 1 | 96 |
| (9) | 1 | 96 |
| (10) | 1 | 97 |
| (11) | 1 | 96 |
| (12) | 1 | 95 |
| A | 1 | 20 |
| B | 1 | 18 |
| C | 1 | 12 |
| D | 1 | 10 |
| E | 1 | 11 |

Test example 5

Controlling test on "Bakanae" disease of rice (*Fusarium moniliforme*)

Unhulled seeds of rice (var., Sasanishiki), infested with benzimidazole-resistant strains of *Fusarium moniliforme*, were dipped for 24 hours in an aqueous dilute solution containing the wettable powder of the test compound prepared according to Formulation example 1 in a prescribed concentration. After air-drying, 50 seeds were sowed on nursery soil and covered with soil. The seedlings were cultivated for 4 weeks in a greenhouse, and the controlling activity was examined. The results are shown in Table 7.

TABLE 7

| Test compound | Application concentration of active ingredient (ppm) | Control of disease (%) |
|---|---|---|
| (1) | 250 | 95 |
| | 125 | 85 |
| (2) | 250 | 95 |
| | 125 | 83 |
| (3) | 250 | 92 |
| | 125 | 83 |
| (4) | 250 | 91 |
| | 125 | 73 |
| (5) | 250 | 90 |
| | 125 | 73 |
| (6) | 250 | 90 |
| | 125 | 78 |
| (7) | 250 | 94 |
| | 125 | 78 |
| (8) | 250 | 93 |
| | 125 | 78 |
| (9) | 250 | 93 |
| | 125 | 79 |
| (10) | 250 | 93 |
| | 125 | 84 |
| (11) | 250 | 92 |
| | 125 | 81 |
| (12) | 250 | 92 |
| | 125 | 84 |
| A | 250 | 7 |
| | 125 | 0 |
| B | 250 | 6 |
| | 125 | 2 |
| C | 250 | 16 |
| | 125 | 10 |
| D | 250 | 16 |
| | 125 | 8 |
| E | 250 | 4 |
| | 125 | 0 |

Test example 6

Controlling test on "Bakanae" disease of rice (*Fusarium moniliforme*)

Unhulled seeds of rice (var., Kinki No. 33), infested with benzimidazole-sensitive strains of *Fusarium moniliforme*, were dipped for 24 hours in an aqueous dilute solution containing the wettable powder of the test compound prepared according to Formulation example 1 in a prescribed concentration. After air-drying, 50 seeds were sowed on nursery soil and covered with soil. The seedlings were cultivated for 4 weeks in a greenhouse, and the controlling activity was examined. The result is shown in Table 8.

TABLE 8

| Test compound | Application concentration of active ingredient (ppm) | Control of disease (%) |
|---|---|---|
| (1) | 250 | 96 |
| | 125 | 86 |
| (2) | 250 | 94 |
| | 125 | 88 |
| (3) | 250 | 92 |
| | 125 | 36 |
| (4) | 250 | 92 |
| | 125 | 40 |
| (5) | 250 | 90 |
| | 125 | 47 |
| (6) | 250 | 90 |
| | 125 | 32 |
| (7) | 250 | 95 |
| | 125 | 37 |
| (8) | 250 | 94 |
| | 125 | 46 |
| (9) | 250 | 93 |

TABLE 8-continued

| Test compound | Application concentration of active ingredient (ppm) | Control of disease (%) |
|---|---|---|
|  | 125 | 35 |
| (10) | 250 | 93 |
|  | 125 | 32 |
| (11) | 250 | 93 |
|  | 125 | 35 |
| (12) | 250 | 92 |
|  | 125 | 35 |
| A | 250 | 50 |
|  | 125 | 11 |
| B | 250 | 61 |
|  | 125 | 8 |
| C | 250 | 52 |
|  | 125 | 11 |
| D | 250 | 43 |
|  | 125 | 4 |
| E | 250 | 49 |
|  | 125 | 8 |

Test example 7

Controlling test on fusarium snow blight of wheat (*Fusarium nivale* f. sp. *graminicola*)

The wettable powder of the test compound prepared according to Formulation example 1 was diluted with water to a prescribed concentration, and sprayed onto wheat seedlings (var., Norin No. 73) at the 3-leaf stage cultivated in plastic pots so that the spray liquid was thoroughly attached to the leaf structure. After air-drying, the seedlings were inoculated by spraying the spore suspension of benzimidazole-resistant strains of *Fusarium nivale* f. sp. *graminicola*. After inoculation, the seedlings were cultivated at 10° C. for 7 days in a highly humid condition and then for 20 days in a constant-temperature room. The controlling activity was then examined. The result is shown in Table 9.

TABLE 9

| Test compound | Application concentration of active ingredient (ppm) | Control of disease (%) |
|---|---|---|
| (1) | 62.5 | 97 |
|  | 15.6 | 80 |
| (2) | 62.5 | 95 |
|  | 15.6 | 80 |
| (3) | 62.5 | 83 |
|  | 15.6 | 50 |
| (4) | 62.5 | 82 |
|  | 15.6 | 53 |
| (5) | 62.5 | 81 |
|  | 15.6 | 53 |
| (6) | 62.5 | 80 |
|  | 15.6 | 52 |
| (7) | 62.5 | 90 |
|  | 15.6 | 51 |
| (8) | 62.5 | 88 |
|  | 15.6 | 51 |
| (9) | 62.5 | 86 |
|  | 15.6 | 51 |
| (10) | 62.5 | 89 |
|  | 15.6 | 54 |
| (11) | 62.5 | 86 |
|  | 15.6 | 58 |
| (12) | 62.5 | 84 |
|  | 15.6 | 55 |
| A | 62.5 | 15 |
|  | 15.6 | 0 |
| B | 62.5 | 13 |
|  | 15.6 | 2 |
| C | 62.5 | 20 |
|  | 15.6 | 0 |
| D | 62.5 | 18 |
|  | 15.6 | 5 |
| E | 62.5 | 7 |
|  | 15.6 | 0 |

Test example 8

Controlling test on fusarium snow blight of wheat (*Fusarium nivale* f. sp. *graminicola*)

The wettable powder of the test compound prepared according to Formulation example 1 was diluted with water to a prescribed concentration, and sprayed onto wheat seedlings (var., Norin No. 73) at the 3-leaf stage cultivated in plastic pots so that the spray liquid was thoroughly attached to the leaf structure. After air-drying, the seedlings were inoculated by spraying the spore suspension of benzimidazole-sensitive strains of *Fusarium nivale* f. sp. *graminicola*. After incoluation, the seedlings were cultivated at 10° C. for 7 days in a highly humid condition and then for 20 days in a constant-temperature room. The controlling activity was then examined. The result is shown in Table 10.

TABLE 10

| Test compound | Application concentration of active ingredient (ppm) | Control of disease (%) |
|---|---|---|
| (1) | 62.5 | 100 |
|  | 15.6 | 85 |
| (2) | 62.5 | 100 |
|  | 15.6 | 88 |
| (3) | 62.5 | 83 |
|  | 15.6 | 40 |
| (4) | 62.5 | 82 |
|  | 15.6 | 48 |
| (5) | 62.5 | 81 |
|  | 15.6 | 46 |
| (6) | 62.5 | 81 |
|  | 15.6 | 41 |
| (7) | 62.5 | 95 |
|  | 15.6 | 41 |
| (8) | 62.5 | 93 |
|  | 15.6 | 48 |
| (9) | 62.5 | 94 |
|  | 15.6 | 43 |
| (10) | 62.5 | 93 |
|  | 15.6 | 43 |
| (11) | 62.5 | 90 |
|  | 15.6 | 43 |
| (12) | 62.5 | 91 |
|  | 15.6 | 47 |
| A | 62.5 | 78 |
|  | 15.6 | 25 |
| B | 62.5 | 80 |
|  | 15.6 | 15 |
| C | 62.5 | 81 |
|  | 15.6 | 20 |
| D | 62.5 | 83 |
|  | 15.6 | 21 |
| E | 62.5 | 72 |
|  | 15.6 | 5 |

Test example 9

Controlling test on fusarium root rot of kidney bean (*Fusarium solani* f. sp. *phaseoli*)

Upland field soil and infested soil containing cultured benzimidazole-sensitive strains of *Fusarium solani* f. sp. *phaseoli* were well mixed and filled in plastic pots. Thereafter, the seeds of kidney bean (var., Nagauzura) dressed with a prescribed amount of the wettable powder of the test compound prepared according to Formulation example 1 were sowed at a rate of 20/pot and covered with soil. The seedlings were cultivated for 4 weeks in a greenhouse, and the controlling activity was examined. The result is shown in Table 11.

TABLE 11

| Test compound | Dosage rate of active ingredient (g/kg of dry seed) | Control of disease (%) |
| --- | --- | --- |
| (1) | 1 | 97 |
| (2) | 1 | 97 |
| (3) | 1 | 91 |
| (4) | 1 | 92 |
| (5) | 1 | 95 |
| (6) | 1 | 93 |
| (7) | 1 | 92 |
| (8) | 1 | 91 |
| (9) | 1 | 93 |
| (10) | 1 | 92 |
| (11) | 1 | 91 |
| (12) | 1 | 90 |
| A | 1 | 23 |
| B | 1 | 19 |
| C | 1 | 13 |
| D | 1 | 12 |

TABLE 11-continued

| Test compound | Dosage rate of active ingredient (g/kg of dry seed) | Control of disease (%) |
| --- | --- | --- |
| E | 1 | 15 |

What is claimed is:

1. A method for controlling Fusarium diseases of living plants or parts of living plants caused by a benzimidazole-resistant strain of Fusarium selected from the group consisting of *Fusarium nivale* f. sp. grimincloa of wheat, and *Fusarium moniliforme* of rice which comprises applying to any of the above-listed Fusaria a fungicidally effective amount of a compound of the formula:

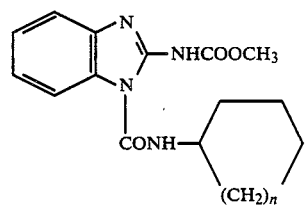

wherein n is 2 or 3.

* * * * *

UNITED STATES PATENT AND TRADEMARK OFFICE
CERTIFICATE OF CORRECTION

PATENT NO. : 4,843,090
DATED : June 27, 1989
INVENTOR(S) : Hiroki TOMIOKA et al

It is certified that error appears in the above-identified patent and that said Letters Patent is hereby corrected as shown below:

Correct the structural formula in Claim 1 to read as follows:

-- 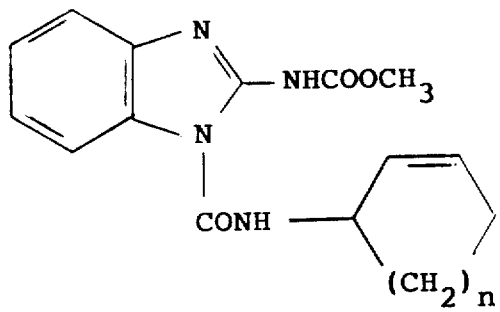 --

Signed and Sealed this

Twenty-eighth Day of May, 1991

*Attest:*

HARRY F. MANBECK, JR.

*Attesting Officer*  Commissioner of Patents and Trademarks